United States Patent [19]
Park

[11] Patent Number: 5,859,302
[45] Date of Patent: Jan. 12, 1999

[54] PROCESSES EMPLOYING REUSABLE ALUMINUM CATALYSTS

[75] Inventor: Won S. Park, Baton Rouge, La.

[73] Assignee: Albemarle Corporation, Richmond, Va.

[21] Appl. No.: 739,225

[22] Filed: Oct. 28, 1996

[51] Int. Cl.$^6$ .............................. C07C 2/68; C07C 1/00; C07C 1/20

[52] U.S. Cl. .................... 585/461; 585/454; 585/459; 585/460; 585/463; 585/466; 585/469

[58] Field of Search ................................ 585/446, 454, 585/459, 460, 461, 462, 463, 466, 469, 406, 422, 472, 428, 477

[56] References Cited

U.S. PATENT DOCUMENTS

| | | | |
|---|---|---|---|
| 2,092,295 | 9/1937 | Peski et al. | 585/461 |
| 2,520,439 | 8/1950 | Sailors | 585/461 |
| 2,882,289 | 4/1959 | Appell | 585/461 |
| 3,275,703 | 9/1966 | Roebuck et al. | 585/460 |
| 4,367,360 | 1/1983 | Gormley | 585/477 |
| 4,980,336 | 12/1990 | Akutsu et al. | 503/209 |
| 5,068,447 | 11/1991 | Gors et al. | 568/309 |
| 5,436,310 | 7/1995 | Dahl et al. | 528/171 |

FOREIGN PATENT DOCUMENTS

| | | | |
|---|---|---|---|
| 4128243 | of 1992 | Japan . | |
| 128243 | 4/1992 | Japan . | |
| 1696416 | 12/1991 | U.S.S.R. | 585/461 |

OTHER PUBLICATIONS

The Effective Synthesis of 1,2–Bis (3,4–dimethylphenyl) ethane; Takahasshi et al., Gakkaishi; vol. 38, No. 5 1995, Nov. 94.

Kirk–Othmer, 3rd Edition, vol. 11, pp. 269–300–Friedel-–Crafts Reactions.

Takahashi et al., "The Effective Synthesis of 1,2–Bis(3, 4–dimethylphenyl)ethane", Sekiyu Gakkaishi, vol. 38, No. 5, 1995, pp. 353–356.

Chauvin et al., "Nonaqueous Ionic Liquids as Reaction Solvents", CHEMTECH Sep. 1995, pp. 26–30.

Olah, "Friedel–Crafts Chemistry", pp. 259 and 566–569 (Wiley & Sons 1973).

Coordination Chemistry of Aluminum–Chapter 6 —Atwood, "Anionic and Cationic Organoaluminum Compounds", pp. 197–219, 1993.

J.L. Atwood et al., Advances in Chemistry Series, No. 150: "Inorganic Compounds with Unusual Properties," Chapter 11 (ACS 1976).

J.L. Atwood, *Inclusion Compounds*—"Liquid Clathrates," pp. 375–405 (Academic Press 1984).

J.L. Atwood, *Recent Developments in Separation Science*, vol. 3, pp. 195–209 (CRC Press 1977).

*Primary Examiner*—Glenn Caldarola
*Assistant Examiner*—Thuan D. Dang
*Attorney, Agent, or Firm*—E. E. Spielman, Jr.

[57] ABSTRACT

Described are novel processes which employ reusable aluminum catalysts in Friedel-Crafts reactions. In one aspect, a novel process for producing a Friedel-Crafts reaction product is described, the process comprising: providing, to a reactor, aromatic reactant and a catalyst system, which system is formed from constituents which comprise (i) an aluminum compound selected from at least one aluminum trihalide, alkyl aluminum halide, or aluminum trialkyl, or a mixture of any two or more of the foregoing, (ii) a salt selected from alkali metal halide, alkaline earth metal halide, alkali metal or alkaline earth metal pseudohalide, quaternary ammonium salt, quaternary phosphonium salt or ternary sulfonium salt, or a mixture of any two or more of the foregoing, and (iii) an aromatic compound which may be the same as or different from the aromatic reactant, the aluminum compound (i), the salt (ii), and the aromatic compound (iii) forming a liquid clathirate which is immiscible in the Friedel-Crafts reaction product and which exhibits Friedel-Crafts catalytic activity. In a preferred embodiment, the liquid clathrate is recovered and reused to catalyze the same or a different Friedel-Crafts reaction.

47 Claims, No Drawings

PROCESSES EMPLOYING REUSABLE ALUMINUM CATALYSTS

TECHNICAL FIELD

This invention pertains to processes employing reusable aluminum catalysts in Friedel-Crafts reactions.

BACKGROUND

Aluminum-containing catalysts are among the most common Lewis acid catalysts employed in Friedel-Craft reactions. Friedel-Craft reactions are reactions which fall within the broader category of electrophylic substitution reactions. There are numerous Friedel-Craft reactions which have been studied and described in the literature. For example, a survey of these reactions is set forth in *Encyclopedia of Chemical Technology*, Volume 11, pp. 269–300 (John Wiley & Sons, 1983). Friedel-Crafts reactions include, but are not limited to, alkylations, cycloalkylations, thioalkylations, acylations, phosphorylations, isomerizations, disproportionations, ortho substitution reactions, condensations, arylations, polymerizations, intermolecular hydride transfer reactions, and the like. In many of these processes it is necessary to separate the aluminum-containing catalyst from the reaction product. Since the reaction product is immiscible or is part of a solution which is immiscible with water or a water solution, the separation can be easily facilitated by treating the reaction mass with water. The water serves two purposes, first, it reacts with the aluminum-containing catalyst, usually a hydrolysis reaction, to form a water soluble species and secondly, it provides a solvent in which this species can be dissolved. The result is a reaction mass having two phases, an organic phase comprised of the reaction product and an aqueous phase containing the water soluble aluminum species. The two phases are then easily separated. While this scheme is widely used, it is not without serious drawbacks. The main two drawbacks are (1) the destruction of the catalyst by the water reaction so that it is deactivated and of no further catalytic use, and (2) the formation of a process waste which is costly to dispose of.

Thus, there exists a need for a technique which allows for the facile separation of an aluminum-containing Friedel-Crafts catalyst from an organic reaction product which does not entail deactivation of the catalyst. With such a technique, the separated catalyst can be recycled for further use, thus attenuating disposal costs.

DESCRIPTION OF THE INVENTION

The present invention is deemed to fulfill this need by providing processes which utilize a catalyst system enabling efficient and substantial recovery of the aluminum catalyst from the reaction mass, without its deactivation, and, optionally, the recovery and efficient use of the recovered aluminum catalyst in one or more subsequent reactions. In particular, this invention provides a process for producing a Friedel-Crafts reaction product, the process comprising:

providing, to a reactor, aromatic reactant and a catalyst system, which system is formed from constituents which comprise,
(i) an aluminum compound selected from aluminum trihalide, alkyl aluminum halide, aluminum trialkyl, or a mixture of any two or more of the foregoing,
(ii) a salt selected from alkali metal halide, alkaline earth metal halide, alkali metal or alkaline earth metal pseudohalide, quaternary ammonium salt, quaternary phosphonium salt, ternary sulfonium salt, or a mixture of any two or more of the foregoing, and
(iii) an aromatic compound which may be the same or different from the aromatic reactant, and
causing the aluminum compound (i), the salt (ii), and the aromatic compound (iii) to form a readily recoverable liquid clathrate which is immiscible in the Friedel-Crafts reaction product and which exhibits Friedel-Crafts catalytic activity.

In a preferred embodiment, the aromatic reactant and the aromatic compound each are an arene (i.e., an aromatic hydrocarbon), which arenes may be the same or different, but are preferably the same.

The immiscibility of the liquid clathrate with the Friedel-Crafts reaction product makes possible the separation of the aluminum compound from the reaction product while at the same time not necessitating the conversion of the aluminum compound to a water soluble species as is preferred by the prior art. As pointed out above. this conversion is not desirable as it causes loss of or deactivation of the aluminum compound's catalytic activity.

In most cases the reactor contents will be highly stirred or agitated during the Friedel-Crafts reaction period. After the reaction period is substantially complete, the two immiscible liquids, i.e., the reaction product and the liquid clathrate, will each be allowed to form their own unitary separate layers. This is accomplished by causing the reaction mixture to become quiescent, under substantially anhydrous conditions, for a period of time sufficient to allow coalescence of the liquid clathrate and consequent formation of the separate, immiscible layers. To cause the mixture to become quiescent, it is typically required that agitation of the reaction mixture be halted so that motion of the mixture's contents is reduced with time to such an extent that formation of the separate, immiscible layers is visible. It is then preferred to separate the two layers. Since the liquid clathrate possesses viable Friedel-Crafts catalytic activity, it is preferably recycled for subsequent catalytic duty. If recycling the liquid clathrate is not desired, it is then preferred that the liquid clathrate be treated to separate the aromatic compound therefrom so that the aluminum compound can be recovered in a non-clathrate form. The treatment may include heat or chemical treatment such as, for example, vacuum distillation followed by vacuum sublimation, or precipitation of the salt complexes using excess aliphatic hydrocarbons followed by vacuum sublimation.

As may now be appreciated, this invention also provides a liquid clathrate composition formed from constituents comprising:
(i) at least one aluminum trihalide,
(ii) at least one salt selected from alkali metal halide alkaline earth metal halide, alkali metal or alkaline earth metal pseudolhalide quaternary ammonium salt, quaternary phosphonium salt, ternary sulfonium salt, or a mixture of any two or more of the foregoing, and
(iii) at least one aromatic compound,
the composition being formed under substantially anhydrous conditions by agitating at least (i), (ii), and (iii) together and causing the mixture to become quiescent at least until a readily recoverable liquid clathrate having Friedel-Crafts catalytic activity is formed.

In another embodiment of this invention, a process for alkylating an aromatic reactant is provided which comprises providing a reaction mass formed from the aromatic reactant and a catalyst system, at least a portion of the system being present as a liquid clathrate formed from constituents which comprise, (i) an aluminum compound selected from at least one aluminum trihalide, alkyl aluminum halide, or aluminum trialkyl, or a mixture of any two or more of the foregoing, (ii) a salt selected from alkali metal halide. alkaline earth metal halide, alkali metal or alkaline earth metal pseudohalide, quaternary ammonium salt, quaternary phosphonium salt, or ternary sulfonium salt, or a mixture of any two or more of the foregoing, and (iii) an aromatic compound which may be the same as or different from the aromatic reactant; and, preferably, after the alkylation is at least substantially complete, recovering at least a portion of the liquid clathrate from the reaction mass and reusing the recovered liquid clathrate to catalyze the same or a different reaction.

In yet another embodiment of this invention, a process is provided for alkylating (A) an alkylatable mononuclear aromatic reactant of the formula:

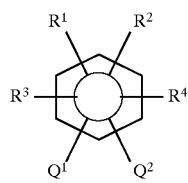

where $Q^1$ and $Q^2$ are the same or different and each is a hydrogen atom, an alkyl group, or an aprotic substituent (e.g., a halogen atom, a hydrocarbyloxy group, a hydrocarbylthio group, a dihydrocarbylamino group, etc.), and $R^1$, $R^2$, $R^3$ and $R^4$ may be the same or different and each is either a hydrogen atom or an alkyl group, at least one of $R^1$, $R^2$, $R^3$ and $R^4$ being a hydrogen atom with (B) a haloalkane having from 1 to 2 halogen atoms, with the proviso that when 2 halogen atoms are present, the respective halogen atoms are bonded to different carbon atoms, the process comprising:

(a) agitating a reaction mixture of the aromatic reactant and the haloalkane in the presence of a catalyst system which is formed from constituents which comprise,
  (i) an aluminum compound selected from aluminum trihalide, alkyl aluminum halide, aluminum trialkyl, or a mixture of any two or more of the foregoing,
  (ii) a salt selected from alkali metal halide, alkaline earth metal halide, alkali metal or alkaline earth metal pseudohalide, quaternary ammonium salt, quaternary phosphonium salt, ternary sultonium salt, or a mixture of any two or more of the foregoing, and
  (iii) an aromatic compound which may be the same or different from the aromatic reactant;

(b) subsequent to (a), causing the formation of a first layer comprised of a liquid clathrate which is formed from constituents comprising (i), (ii) and (iii), which is immniscible in the Friedel-Crafts reaction product, and which exhibits Friedel-Crafts catalytic activity, and a second layer comprised of the alkylated aromatic reactant; and (c) optionally, recovering at least a portion of the liquid clathrate layer for use in a subsequent Friedel-Crafts reaction mixture to provide at least a part of the catalyst needs for such subsequent reaction mixture.

In a preferred embodiment, the aromatic reactant and the aromatic compound each are an arene, which arenes may be the same or different, but are preferably the same.

This invention further provides a process for enriching the 1,2-bis(3,4-dimethylphenyl)ethane content of a mixture of bis(dimethylphenyl)ethanes and/or over-alkylated co-products. The process comprises agitating the mixture in the presence of an aluminum-containing Friedel-Crafts catalyst, at least a portion of the Friedel-Crafts catalyst being present as part of a liquid clathrate formed with an arene and a salt selected from alkali metal halide, alkaline earth metal halide, alkali metal or alkaline earth metal pseudohalide, quaternary ammonium salt, quaternary phosphonium salt, ternary sulfonium salt, or a mixture of any two or more of the foregoing. After the reaction is at least substantially complete, preferably recovering at least a portion of the liquid clathrate from the mixture and preferably reusing the recovered liquid clathrate to catalyze the same or a different reaction.

The catalytic system used in the processes of this invention is, as before noted, formed at least partially from an aluminum compound (broadly defined as a Friedel-Crafts catalyst), a salt (broadly defined as any salt capable of forming a complex with the aluminum compound) and an aromatic compound (broadly defined as any aromatic compound capable of forming a liquid clathrate with the aluminum compound and salt). The catalytic system can be formed separately from the aromatic reactant or reaction mixture, or, more preferably, it can be formed in situ with the aromatic reactant or reaction mixture. To accomplish the former, the catalytic system constituents are mixed together and then added to the aromatic reactant, etc. In the case of the latter, the constituents are each added, in any sequence, to the aromatic reactant or reaction reactor. The catalytic efficacy of the catalytic system during the Friedel-Crafts reaction can be the result of an individual constituent's catalytic activity, e.g., the aluminum compound, and/or the result of the catalytic activity of a combination of any two or more of the constituents, e.g., the liquid clathrate. It is theorized. through the processes of this invention are not to be so limited, that the catalytic activity during the reaction period is provided by the aluminum compound and the liquid clathrate. When speaking of the catalytic activity of the liquid clathrate, it is meant to include, such as they exist, both the activity of the liquid clathrate itself and any activity of a constituent of the liquid clathrate.

The aluminum compounds used in the practice of this invention are any of those aluminum-containing compounds which are considered by the art to be in and of themselves Friedel-Crafts catalysts. Also the aluminum compounds have to be capable of forming the clathrates of this invention. As before noted, such compounds can be selected from aluminum trihalide, alkyl aluminum halide, aluminum trialkyl or mixtures thereof. Suitable aluminum trihalides include aluminum trichloride, aluminum tribromide, aluminum tritluoride, and aluminum triuodide, as well as mixtures of such compounds.

The aluminum trihalides are preferred for use in processes of this invention, especially those processes involving the alkylation of arenes, e.g., the alkylation of an arene with a dihaloalkane. Especially preferred are aluminum trichloride, aluminum tribromide and mixtures thereof. Aluminum trifloride and triiodide are suitable, but are not generally preferred.

Suitable alkyl aluminum halides may have 1 or 2 branched or straight-chain alkyl groups which may be the same or different, each having from 1 to about 10 carbon atoms. Examples of such alkyl aluminum halides include dimethylaluminum chloride, methylaluminum dichloride, dimethylaluminum bromide, methylaluminum dibromide, dimethylaluminum iodide, methylaluminum diiodide, dimethylaluminum fluoride, methylaluminum difluoride, diethylaluminum chloride, ethylaluminum dichloride, diethylaluminum bromide, ethylaluminum dibromide di-n-propylaluminum chloride, n-propylaluminum dichloride, and the like, including higher homologs and mixtures of such compounds.

Suitable aluminum trialkyl compounds for use in the practice of this invention have alkyl groups which may be the same or different, and may have branched or straight-chain alkyl groups each having from 1 to about 10 carbon atoms. Suitable aluminum trialkyl compounds with straight-chain alkyl groups may include, for example, trimetlhylaluminum, triethylaluminum, tripropylaluminum, tributylaluminum, tripentylaluminum, trihexylaluminum, triheptylaluminum, trioctylaluminum, trinonylaluminum, tridecylaluminum, tris(dodecyl)aluminum, tris(tetradecyl) aluminum, and the like, including higher homologs and mixtures of such compounds. Suitable aluminum trialkyl compounds with branched alkyl groups include, for example, triisopropylaluminum, triisobutylaluminum, tri(2-methylpentyl)aluminum, tri(3-methylpentyl)aluminum, tri(4-methylpentyl)aluminum, tri(2-diethylhexyl)aluminum, tri(3-ethylhexyl)aluminum, tri(4-ethylhexyl)aluminum, tri(2,4-diethylhexyl)aluminum, and the like, including higher homologs and mixtures of such compounds. In certain embodiments of this invention, the aluminum compound is preferably an aluminum trihalide, most preferably aluminum trichloride.

The salt which is used in the practice of this invention is any salt which is capable of forming a complex with the aluminum compound, which complex will form a liquid clathrate with the aromatic compound. Suitable are salts selected from alkali metal halide, alkaline earth metal halide, alkali metal or alkaline earth metal pseudohalide, quaternary ammonium salt, quaternary phosphonium salt, ternary sulfonium salt, or any mixture thereof. Specific examples of suitable salts include, sodium chloride, magnesium chloride, potassium iodide, potassium bromide, calcium chloride, beryllium fluoride, strontium iodide, barium bromide, potassium nitride, cesium nitride, potassium nitrate, cesium nitrate, tetramethylammonium chloride, triethylmethylammonium bromide, triethylmethylammonium chloride, tetramethylammonium bromide, dimethylpyrrolidinium chloride, trimethylethylammonium chloride, tetramethylphosphonim bromide, triethylmethylphosphonium bromide, triethylmethylphosphoninum chloride, trimethylsulfonium chloride, tetra-n-butylammonium bromide, and the like, including higher homologs and mixtures of such compounds. Of course, the halide component in each of these compounds may be either chloride, bromide, fluoride, or iodide, with bromide or chloride being preferred. For a more detailed discussion of pseudohalides, see Atwood, J. L., *Inclusion Compounds*, Vol. 1, pp. 195–209 (Academic Press 1984), the disclosure of which is fully incorporated herein. In certain embodiments of this invention, the salt is preferably a quaternary ammonium salt, most preferably a quaternary ammonium bromide.

The aromatic compound used in forming the catalyst system is any of which is capable of forming the desired liquid clathrate in combination with the aluminum compound and the salt. It is preferred that the aromatic compound of the catalyst system be the same as the aromatic reactant. In this way, contamination of the reaction product is diminished and the process is simplified. If the aromatic compound and aromatic reactant are to be different, then the aromatic compound of the catalyst system should be chosen so that it is benign to the process. For examples of suitable aromatic compounds, reference is made to the recitation below of suitable aromatic reactants. In preferred embodiments of the invention, the aromatic compound used in forming the catalyst system is an arene. Liquid clathrates will be best formed from mononuclear arenes such as benzene, toluene, xylene, mesitylene, ethylbenzene, cumene, cymene, and the like, with o-xylene being particularly preferred.

Quantitatively, the amount of catalytic system used should be that amount which will provide enough Friedel-Crafts catalytic activity to insure a useful and efficient process. The mole ratio of aluminum compound to aromatic (compound and reactant) is within the range of from about 0.001:1 to about 0.5:1 More preferred is the ratio of from about 0.1:1 to about 0.2:1. It is preferred to use a molar ratio of aluminum compound to reagent which is within the range of from about 0.01:1 to about 3:1, and most preferably within the range of from about 0.1:1 to about 1:1. To provide sufficient catalytic activity to the process while permitting recovery of the aluminum chloride via the liquid clathrate, the mole ratio of aluminum compound to salt is preferably within the range of from about 0.01 to about 2, and more preferably within the range of from about 0.1 to about 2.

The aromatic reactant of this invention, as well as the aromatic liquid clathrate constituent (which may be the same as or different from the aromatic reactant), may include monocyclic and polycyclic aromatic compounds, and may include, for example, aromatic hydrocarbons and aromatic compounds having aprotic substituents. For example, aprotically substituted aromatic compounds such as aromatic ethers, aryl sulfides, aromatic nitriles, arylhalides and the like are useful. Specific examples of suitable aromatic hydrocarbons include benzene, cumene, cymene, mesitylene, styrene, toluene, xylene, indene, naphthalene, biphenyl, acenaphthene, fluorene, 1,2-bis(phenyl)ethane, and the like. Specific examples of suitable aromatic compounds having aprotic substituents include anisole, ethyl phenyl ether, tert-butyl phenyl ether, cyclopropyl phenyl ether, p-dimiethoxybenzene, p-bromoanisole, p-chloroanisole, N,N-dimethylaniline, N,N-dimethyl-p-toluidene, N,N-diethylaniline, N-ethyl-N-methylaniline, p-chloro-N,N-dimethylaniline, bromobenzene, chlorobenzene, 1-chloronaphthalene, 2-chloronaphthalene, 1,4-dichlorobenzene, 2,3-dichliorotoluene and the like. In preferred embodiments, the aromatic reactant and the aromatic compound forming part of the liquid clathrate are selected from the preferred arenes listed above for liquid clathrate formation with alkylatable monocyclic arenes fron the benzene series such as xylene for example, being particularly preferred. By alkylatable is meant that the aromatic ring contains at least one carbon atom lhaving a hydrogen substituent available for and susceptible to alkylation. Generally speaking, the aromatic compounds will contain up to about 40 carbon atoms per molecule.

In addition, the aromatic reactant of this invention may also include an alkylated aromatic compound, an isomeric mixture of alkylated aromatic compounds, an over-alkylated aromatic compound, a mixture of over-alkylated aromatic compounds or a mixture of any two or more of the foregoing. (By "over-alkylated aromatic compounds" it is meant that the compound contains at least one more aromatic and/or haloalkyl group constituent than is desired, the excess aromatic constituent(s), when present, being each bonded to the rest of the molecule by at least one alkyl substituting group.) In these cases, the practitioner may use the processes of this invention to obtain a reaction product which is more pure in a particular alkylated aromatic compound or obtain a less-alkylated aromatic compound, preferably a single isomeric product of the formula Ar-R-Ar, where Ar is an arene or an arene substituted by one or more aprotic groups and R is an alkylene group having at least 2 carbon atoms. For example, a process of this invention can be used to enhance the 1,2-bis(3,4-dimethylphenyl)-ethane content of a mix containing a lesser amount of same and, as an aromatic reactant, any one or more of 1,2-bis(2,3-dimethylphenyl) ethane, 1,2-bis(2,4-dimethylphenyl)ethane, 1,2-bis(3,5-dimethylphenyl)ethane, and 1-(3,4-dimethylphenyl)-2-(3,5-dimethylphenyl)ethane. A further example is that in which the aromatic reactant includes at least one over-alkylated aromatic compound, such as bis(xylylethyl)xylenes. Such xylenes are exemplified by 1,4-bis[2-(2,3-xylyl)ethyl]-2,3-xylene, 1,4-bis[2-(3,4-xylyl)ethyl]-2,3-xylene, 1,5-bis[2-(3, 4-xylyl)ethyl]-2,3-xylene, and the like. These xylenes are readily converted to 1,2-bis(3,4-dimethylphenyl)ethane by the processes of this invention. Though an initial concentration of 1,2-bis(3,4-dimethylphenyl)ethanie can be present in any of these reaction masses, it is not necessary for the purposes of this invention. When the processes of this invention are so used, the aromatic compound used to form the clathrate will need to be one which is different from the alkylated aromatic reactant. In this regard, benzene, toluene, xylene, mesitylene, ethylbenzene, cumene, cymene and the like are preferred. It is especially useful to choose the aromatic compound for clathrate formation so that it also can be alkylated to produce the desired product. For example, when the desired product is 1,2-bis(3,4-dimethylphenyl)ethane, o-xylene would be a most preferred liquid clathrate-forming aromatic compound for use in the process.

The other reagent used in the Friedel-Crafts reaction of this invention provides the substituting group and is capable of forming a carbocation or carbocation-like complex with an aluminum containing Friedel-Crafts catalyst, e.g., $AlCl_3$. The carbocation acts as an electrophile which can attack an aromatic ring site to effect the substitution. Selection of this reagent is based upon the desired Friedel-Crafts reaction product. For example, if the Friedel-Crafts reaction is to be an alkylation, then haloalkanies are suitable and preferred. Exemplary of reagents suitable for producing alkylated monoarene products are ethlylchloride, propylchloride, butylchloride, methylbromide, ethylbromide, ethyliodide, octylchloride, n-decylbromide, tert-butylchloride, and analogous monohaloalkanes. If the Friedel-Crafts reaction product sought is a diarene product, e.g., diphenylethane and 1,2-bis(3,4-dimethylphenyl)ethane, then the following reagents may be used, ethylene dichloride, ethylene dibromide, 1,2-dichloropropane, 1,3-dichloropropane, 1,3-dichlorobutane 1,4-dibromobutane, 1,6-dichlorohexane, 1,7-dibromoheptane, 1,8-dibromooctane, 1,4-diiodobutane, 1,4-dichlorooctane and analogous dihaloalkanes. A preferred dihaloalkane is ethylene dichloride. Generally speaking, the haloalkanes will contain up to about 18 carbon atoms per molecule.

It is suitable to provide from about 2 to about 20 and, preferably from about 2 to about 10 times the stoichiometric amount of aromatic reactant to the reaction mass. Such an excess is beneficial to provide organic solvent to the reaction mass and to reduce by-product formation. Further, if the aromatic compound used in forming the catalyst system is to be the same as the aromatic reactant, then some of the excess aromatic reactant can be used for that purpose. If the reaction product is a monocylic aromatic compound having a single Friedel-Crafts substitution, then the stoichiometric molar relationship between the aromatic reactant and reagent is 1:1. If, however, the reaction product is a dicyclic aromatic compound, such as diphenylethane, then the molar stoichiometric relationship will be 2:1. Other relationships can be easily determined by reference to the reaction equations of the particular process being considered. Generally speaking, when preparing, 1,2-bis(3,4-dimethylphenyl) ethane from o-xylene and ethylene dichloride, the molar ratio of aromatic reactant to haloalkane should be within the range of from about 2:1 to about 20:1. When the reaction product is diphenylethane the molar ratio of benzene to ethylene dichloride should be within the range of from about 2:1 to about 20:1.

The reaction conditions and duration in the various processes of this invention can vary widely, depending upon the starting materials used and the nature and amount of the desired end product. Generally, the reaction temperature employed in the processes of this invention may range from about 0° to about 200° C. When the desired product is a diarene, the preferred reaction temperature is within the range of from about 0° to about 150° C. Most preferably, the temperature range is from about 25° to about 100° C. When the desired reaction product is 1,2-bis(3,4-dimethylphenyl) ethane, the preferred temperature is within the range of from about 50° to about 100° C. When the desired reaction product is diphenylethane, a reaction temperature of from about 0° to about 120° C. is preferred. The processes of this invention are not particularly pressure dependent. It is preferred that the pressure be such that the reaction mass is not in a boiling state. The pressure used in the processes of this invention may range from about atmospheric up to about 250 psia and preferably up to about 200 psia. The more preferred pressures are atmospheric or near-atmospheric (14–20 psia) pressures. The processes of this invention may be conducted as either continuous, semi-continuous or batch reactions. The processes should also be carried out under substantially anhydrous conditions as water is destructive of the aluminum compound constituent of the catalyst system and may be destructive of the formed liquid clathrate. Some level of moisture is tolerable so long as that level does not deleteriously effect the process. It is preferred to run the processes of this invention under a dry inert atmosphere, such as that supplied by dry nitrogen, argon, etc. The reaction periods may vary widely depending upon the results desired, but will typically be carried out for a time of from about 1 to 24 hours. The reaction periods should only be that approximate amount of time needed to maximize product yield without incurring undue process inefficiency. The process time can be determined by monitoring the process for the cessation of formation of substitution by-products. In the case where a haloalkane is the reagent of choice, the substitution by-product will be a hydrogen halide, e.g., ethylene dichloride will yield HCl as the substitution by-product. Reaction periods for producing diphenylethane and 1,2-bis(3,4-dimethylphenyl)ethane are preferably about 10 hours or less.

The aromatic reactant, the reagent, and the catalyst system can be provided to the reactor in any order. However, it is preferred to provide the aromatic reactant first if a portion thereof is going to provide the aromatic compound constituent of the catalyst system. Thus, in this case the aromatic reactant is added first, the catalyst system second and the reagent third or contemporaneously with the second addition.

To insure that the reagents and catalyst system used in the process of this invention are well mixed during the reaction period, the reaction mass needs to be kept in a well stirred or agitated condition. After the reaction period has lapsed, the reaction mass is no longer stirred or agitated and the separate organic layers are allowed to form.

The following examples serve to illustrate this inventions but do not limit it. All parts are by weight unless otherwise indicated.

EXAMPLE 1

A reaction of 12-fold excess o-xylene (12.0 mols, 1,274 gm) with ethylene dichloride (1.0 mol, 99 gm) catalyzed by one equivalent of aluminum trichloride (1.0 mol, 133 gm) in the presence of one-half equivalent of tetra-n-butylammonium bromide (0.5 mol, 161 gm) was carried out under a nitrogen atmosphere at 50° C. for 9 hours with efficient stirring. When the stirring was stopped thereafter and while the mixture became quiescent immediate separation of two organic phases occurred indicating formation of a liquid clathrate. The top organic layer was decanted off via a double-ended needle and washed with 5% aqueous sodium hydroxide to remove any remaining HCl and aluminum trichloride. The products, bis-(dimethylphenyl)ethanes, were isolated by evaporating solvent of the organic layer. Upon recrystallization of the products in alcohol, 1,2-bis(3,4-dimethylphenyl)ethane was obtained in good selectivity (61–68%) and yields (41–58%). The bottom layer was subsequently used as the catalyst system for four more cycles of the same reaction.

EXAMPLE 2

A reaction of 12-fold excess benzene (4.5 mols, 350 gm) with ethylene dichloride (0.37 mol, 36.9 gm) catalyzed by one-half equivalent of aluminum trichloride (0.186 mol, 24.9 gill) in the presence of one-quarter equivalent of tri-n-butylammonium bromide (0.093 mol, 30.1 gm) was carried out under a nitrogen atmosphere at 70° C. for 9 hours with efficient stirring. When the stirring was stopped thereafter and while the mixture became quiescent, immediate separation of two organic phases occurred, indicating formation of a liquid clathrate. The top organic layer containing 1–2% of total aluminum trichloride added, was decanted off via a double-ended needle and washed with 5% aqueous sodium hydroxide. The product, diphenylethane, was isolated by distillation in good yield (75%) and selectivity (85%) toward formation of diphenylethane versus over-alkylated co-products. The bottom liquid clathrate layer was a dark, viscous liquid immiscible in organic solvent and was used as the catalyst for another cycle of the same reaction. In a recycled run, a 55% yield of diphenylethane was obtained without supplementing aluminum chloride catalyst after 9 hours reaction at 70° C.

EXAMPLE 3

A total of 23.4 grams of a residue isolated from the mother liquor of the reaction set forth above as Example 1 containing mainly 1,2-bis-(dimethylphenyl)ethanes, over-alkylated co-products, and only 0.13 GC area % of 1,2-bis(3,4-dimethylphenyl)ethane was treated with 13.3 grams of aluminum trichloride, 16.2 grams of tetra-n-butylammonium bromide and 150 mL of o-xylene for 9 hours at 50° C. with efficient stirring. When the stirring was stopped thereafter and while the mixture became quiescent, immediate separation of two organic phases occurred, indicating formation of a liquid clathrate. The isomerized product isolated from the top layer contained 69 GC area % of 1,2-bis(3,4-dimethylphenyl)ethane with a demonstrated conversion of the 1,2-bis-(dimethylphenyl)ethanes mixture and over-alkylated co-products to the desired 1,2-bis(3,4-dimethylphenyl)ethane.

Even though the liquid clathrate formed and/or used in the practice of this invention is typically immiscible in organic solvent, the liquid clathrate exhibits efficient catalytic activity when used as the catalyst system in subsequent reactions. The liquid clathrate will often have a darker coloration which distinguishes it from the top organic layer. As can be seen from the above examples, the liquid clathrate contains substantially all of the aluminum catalyst, thereby providing a platform from efficient recovery of the catalyst from the reaction mass, and efficient recycle of substantially all of the aluminum catalyst used in the initial reaction.

It is to be clearly understood and appreciated that in the specification and claims hereof, all references to substances used in the process relate to the initial identity of the material being used, and such references do not in any way require that during the process the substances must maintain that identity until the instant, if any, that a chemical transformation occurs to form a different substance. In short, once two or more of the identified materials are brought into contact with or proximity to each other, whether under reaction conditions or not, one or more of them may undergo a change in identity as compared to their original identity, and such change or changes are encompassed by the claims hereof as long as the end results of the overall process are as described herein.

Each and every patent, patent application, or other publication referred to above is incorporated by reference as if fully set forth herein. This invention is susceptible to considerable variation in its practice. Therefore, the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for producing a Friedel-Crafts reaction product, the process comprising: providing, to a reactor, aromatic reactant and a catalyst system, which system is formed from constituents which comprise,
    (i) an aluminum compound selected from at least one aluminum trihalide, alkyl aluminum halide, or aluminum trialkyl, or a mixture of any two or more of the foregoing,
    (ii) a salt selected from alkali metal halide, alkaline earth metal halide, alkali metal or alkaline earth metal pseudohalide, quaternary ammonium salt, quaternary phosphonium salt, or ternary sulfonium salt, or a mixture of any two or more of the foregoing, and
    (iii) an aromatic compound which may be the same as or different from the aromatic reactant, and
causing the aluminum compound (i), the salt (ii), and the aromatic compound (iii) to form a readily recoverable liquid clathrate which is immiscible in the Friedel-Crafts reaction product and which exhibits Friedel-Crafts catalytic activity.

2. A process in accordance with claim 1 wherein the aromatic compound and the aromatic reactant each are an arene.

3. A process in accordance with claim 2 wherein the aromatic compound and the aromatic reactant each are the same arene.

4. A process in accordance with claim 1 wherein the Friedel-Crafts reaction is an alkylation reaction.

5. A process in accordance with claim 1 wherein the aluminum compound is at least one aluminum trihalide.

6. A process in accordance with claim 5 wherein the aluminum trihalide is aluminum trichloride.

7. A process in accordance with claim 1 wherein the salt is at least one quaternary ammonium salt.

8. A process in accordance with claim 7 wherein the quaternary ammonium salt is tetra-n-butylammonium bromide.

9. A process in accordance with claim 1 wherein the liquid clathrate is recovered and reused to catalyze the same or a different Friedel-Crafts reaction.

10. A process for alkylating an aromatic reactant, which process comprises: providing a reaction mass formed from the aromatic reactant and a catalyst system, at least a portion the system being present as a liquid clathrate formed from constituents which comprise, (i) an aluminum compound selected from at least one aluminum trihalide, alkyl aluminum halide, or aluminum trialkyl, or a mixture of any two or more of the foregoing, (ii) a salt selected from alkali metal halide, alkaline earth metal halide, alkali metal or alkaline earth metal pseudohalide, quaternary ammonium salt, quaternary phosphonium salt, or ternary sulfonium salt, or a mixture of any two or more of the foregoing, and (iii) an aromatic compound which may be the same as or different from the aromatic reactant.

11. A process in accordance with claim 10 further comprising, after the alkylation is at least substantially complete, recovering at least a portion of the clathrate from the reaction mass and reusing the recovered clathrate to catalyze the same or a different reaction.

12. A process in accordance with claim 10 wherein the aluminum compound is at least one aluminum trihalide.

13. A process in accordance with claim 12 wherein the aluminum trihalide is aluminum trichloride.

14. A process in accordance with claim 10 wherein the salt is at least one quaternary ammonium salt.

15. A process in accordance with claim 14 wherein the quaternary ammonium salt is tetra-n-butylammonium bromide.

16. A process for alkylating (A) an alkylatable mononuclear aromatic reactant of the formula:

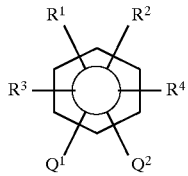

where $Q^1$ and $Q^2$ are the same or different and each is a hydrogen atom, an alkyl group, or an aprotic substituent, and $R^1$, $R^2$, $R^3$ and $R^4$ may be the same or different and each is either a hydrogen atom or an alkyl group, at least one of $R^1$, $R^2$, $R^3$ and $R^4$ being a hydrogen atom, with (B) a haloalkane having from 1 to 2 halogen atoms, with the proviso that when 2 halogen atoms are present, the respective halogen atoms are bonded to different carbon atoms, the process comprising:

(a) agitating a reaction mixture of the aromatic reactant and the haloalkane in the presence of a catalyst system which is formed from constituents which comprise,
  (i) an aluminum compound comprising, at least one aluminum trihalide, alkyl aluminum halide, aluminum trialkyl, or a mixture of any two or more of the foregoing,
  (ii) a salt selected from alkali metal halide, alkaline earth metal halide, alkali metal or alkaline earth metal pseudohalide, quaternary ammonium salt, quaternary phosphonium salt, ternary sulfonium salt, or a mixture of any two or more of the foregoing, and
  (iii) an aromatic compound which may be the same as or different from the aromatic reactant;

(b) subsequent to (a), causing the formation of a first layer comprised of a liquid clathrate which is formed from constituents comprising, (i), (ii) and (iii), which is immiscible in the Friedel-Crafts reaction product, and which exhibits Friedel-Crafts catalytic activity, and a second layer comprised of the alkylated aromatic reactant; and (c) optionally, recovering at least a portion of the liquid clathrate layer for use in a subsequent Friedel-Crafts reaction mixture to provide at least a part of the catalyst needs for such subsequent reaction mixture.

17. A process in accordance with claim 16 wherein the aromatic reactant and the aromatic compound are each an arene.

18. A process in accordance with claim 17 wherein the aromatic reactant and the aromatic compound are each the same arene.

19. A process in accordance with claim 16 wherein the aluminum compound is an aluminum trihalide.

20. A process in accordance with claim 19 wherein the aluminum trihalide is aluminum trichloride.

21. A process in accordance with claim 16 wherein the salt is a quaternary ammonium salt.

22. A process in accordance with claim 21 wherein the quaternary ammonium salt is tetraalkyl ammonium bromide or tetraalkyl ammonium chloride.

23. A process in accordance with claim 22 wherein the aluminum compound is aluminum trichloride.

24. A process in accordance with claim 16 wherein the haloalkyl is a dihaloalkane.

25. A process in accordance with claim 24 wherein the dihaloalkanie is ethylene dichloride.

26. A process in accordance with claim 16 wherein the aromatic compound is an aromatic hydrocarbon.

27. A process in accordance with claim 26 wherein the aromatic hydrocarbon is o-xylene.

28. A process in accordance with claim 27 wherein the haloalkane is a dihaloalkane.

29. A process in accordance with claim 28 wherein the dihaloalkane is ethylene dichloride.

30. A process in accordance with claim 29 wherein the aluminum compound is an aluminum trihalide, the salt of a tetra-n-butylanmmonium halide, the reaction mixture in step (a) is maintained at a temperature in the range of about 0° to about 150° C. and a pressure in the range of about 14 to about 200 psia, and the alkylated reaction product is at least one 1,2-bis(3,4-dimethylphenyl)ethane.

31. A process in accordance with claim 26 wherein the aromatic hydrocarbon is benzene.

32. A process in accordance with claim 31 wherein the haloalkane is a dihaloalkane.

33. A process in accordance with claim 32 wherein the dihaloalkane is ethylene dichloride.

34. A process in accordance with claim 33 wherein the aluminum compound is an aluminum trihalide, the salt is a tetra-n-butylammonium halide, the reaction mixture in step (a) is maintained at a temperature in the range of about 0° to about 120° C. and a pressure in the range of about 14 to about 200 psia, and the alkylated reaction product is at least one diphenylethane.

35. A process for converting one or more aromatic reactants selected from at least two or more isomeric forms of an alkylated aromatic compound, at least one over-alkylated aromatic compound, or a mixture of any two or more of the foregoing, into a single isomeric product of the formula Ar—R—Ar, where Ar is an arene or an arene substituted by one or more aprotic groups and R is an alkylene group having at least 2 carbon atoms, the process comprising agitating the reaction mass in the presence of a catalyst system, at least a portion of the system being present as a liquid clathrate formed from constituents which comprise,
  (i) an aluminum compound selected from at least one aluminum trihalide, alkyl aluminum halide, or aluminum trialkyl, or a mixture of any two or more of the foregoing, (ii) a salt selected from alkali metal halide, alkaline earth metal halide, alkali metal or alkaline earth metal pseudohalide, quaternary ammonium salt, quaternary phosphonium salt, or ternary sulfonium salt, or a mixture of any two or more of the foregoing, and (iii) an aromatic compound which may be the same as or different from any one of the aromatic reactants.

36. A process in accordance with claim 35 further comprising, after the reaction is at least substantially complete, recovering at least a portion of the clathrate from the reaction mass and reusing the recovered clathrate to catalyze the same or a different reaction.

37. A process in accordance with claim 35 wherein Ar is a xylyl group and R is an ethylene group.

38. A process in accordance with claim 37 wherein the isomeric product is 1,2-bis(3,4-dimethylphenyl)ethane.

39. A process for enriching the 1,2-bis(3,4-dimethylphenyl)ethane content of a mixture of bis(dimethylphenyl)ethanes, the process comprising: agitating the mixture in the presence of a catalyst system, at least a portion of the system being present as a liquid clathrate formed from constituents which comprise, (i) an aluminum compound selected from at least one aluminum trihalide, alkyl aluminum halide, or aluminum trialkyl, or a mixture of any two or more of the foregoing, (ii) a salt selected from alkali metal halide, alkaline earth metal halide, alkali metal or alkaline earth metal pseudohalide, quaternary ammonium salt, quaternary phosphonium salt, or ternary sulfonium salt, or a mixture of any two or more of the foregoing, and (iii) an aromatic compound which may be the same as or different from any one of the aromatic reactants.

40. A process in accordance with claim 39 further comprising, after the reaction is at least substantially complete, recovering at least a portion of the clathate from the mixture and reusing the recovered clathrate to catalyze the same or a different reaction.

41. A process in accordance with claim 39 wherein the aluminum-containing catalyst is an aluminum trihalide.

42. A process in accordance with claim 41 wherein the aluminum trihalide is aluminum trichloride.

43. A process in accordance with claim 39 wherein the salt is a quaternary ammonium salt.

44. A process in accordance with claim 43 wherein the quaternary ammonium salt is tetraalkyl ammonium bromide or tetraalkyl ammonium chloride.

45. A process in accordance with claim 44 wherein the aluminum-containing catalyst is aluminum trichloride.

46. A process for the production of 1,2-bis(3,4-dimethylphenyl)ethane, the process comprising:

(a) agitating a reaction mixture comprised of o-xylene and a dihaloethlane in the presence of a first catalyst system which is formed from constituents which comprise, (i) an aluminum compound selected from at least one aluminum trihalide, alkyl aluminum halide, aluminum trialkyl, or a mixture of any two or more of the foregoing, (ii) a salt selected from alkali metal halide alkaline earth metal halide, alkali metal or alkaline earth metal pseudohalide, quaternary ammonium salt, quaternary phosphonium salt, ternary sulfonium salt, or a mixture of any two or more of the foregoing, and (iii) o-xylene; to form a reaction product;

(b) causing the formation of the reaction product of a first layer comprised of a liquid clathrate which is formed from constituents comprising (i), (ii) and (iii), which is immiscible in the reaction product, and which exhibits Friedel-Crafts catalytic activity, and a second layer comprised of alkylated o-xylene;

(c) separating the first layer and the second layer from each other;

(d) recovering 1,2-bis(3,4-dimethylphenyl)ethane from the second layer;

(e) thereafter, agitating at least a portion of the second layer with at least a portion of the liquid clathrate and optionally a second catalyst system which is formed from constituents which comprise, (i) at least an aluminum compound comprising at least one aluminum trihalide, alkyl aluminum halide, aluminum trialkyl, or a mixture of any two or more of the foregoing, and optionally, (ii) a salt selected from alkali metal halide, alkaline earth metal halide, alkali metal or alkaline earth metal pseudohalide, quaternary ammonium salt, quaternary phosphonium salt, terniary sulfonium salt, or a mixture of any two or more of the foregoing, and (iii) o-xylene, and repeating steps (b), (c) and (d).

47. The process of claim 46 wherein the aluminum compound in (a)(i) and (e)(i) is aluminum trichloride, and wherein the salt in (a)(ii) and (e)(ii) is a quaternary ammonium salt.

* * * * *